United States Patent [19]
Rothan

[11] Patent Number: 5,913,416
[45] Date of Patent: Jun. 22, 1999

[54] FOLDING VISOR AND CASE APPARATUS FOR EYEGLASSES

[76] Inventor: Matthew J. Rothan, 10801 SW. 78th Ave., Miami, Fla. 33156

[21] Appl. No.: 08/961,785

[22] Filed: Oct. 31, 1997

[51] Int. Cl.[6] .................................................. A45C 11/04
[52] U.S. Cl. ........................................ 206/5; 206/6; 2/13
[58] Field of Search ................................ 206/5, 6; 2/13, 2/909

[56] References Cited

U.S. PATENT DOCUMENTS

| | | | |
|---|---|---|---|
| 2,541,242 | 2/1951 | Grove | 2/13 |
| 2,557,552 | 6/1951 | Martin | 206/5 |
| 2,890,458 | 6/1959 | Hammond | 2/13 |
| 3,629,870 | 12/1971 | Paisley | 2/13 |
| 4,543,667 | 10/1985 | Garbutt | 2/13 |
| 4,606,453 | 8/1986 | Burns | 206/5 |
| 4,945,573 | 8/1990 | Landis | 2/9 |
| 5,113,529 | 5/1992 | Carr | 2/13 |
| 5,299,682 | 4/1994 | Tatar | 206/5 |
| 5,339,119 | 8/1994 | Gardner | 351/158 |
| 5,388,269 | 2/1995 | Griffin | 2/13 |
| 5,493,349 | 2/1996 | Barhydt et al. | 206/6 |
| 5,553,321 | 9/1996 | Cassel | 2/13 |

Primary Examiner—David T. Fidel
Attorney, Agent, or Firm—Frank L. Kubler

[57] ABSTRACT

A folding visor and case apparatus for eyeglasses which include an eyeglass lens frame containing eyeglass lenses and eyeglass arms hingedly connected to the eyeglass lens frame includes two substantially rigid side panels; a substantially rigid sun shield panel extending between the side panels and having two sun shield panel lateral ends; a hinged linkage panel assembly connecting each of the side panels to a lateral end of the sun shield panel, each of the linkage panel assemblies including a series of at least first and last panel sections interconnected with hinges, the first panel section in the series being pivotally connected to an edge of one of the side panels and the last panel section in the series being pivotally connected at one of the sun shield panel lateral ends; where the side panels each include an eyeglass arm attachment structure for operationally interconnecting the eyeglasses and the apparatus to open and close substantially in unison, so that opening the apparatus deploys the sun shield panel over the eyeglass lenses to function as a visor and closing the apparatus causes the side and sun shield panels to envelope the eyeglasses to function as a protective case.

8 Claims, 3 Drawing Sheets

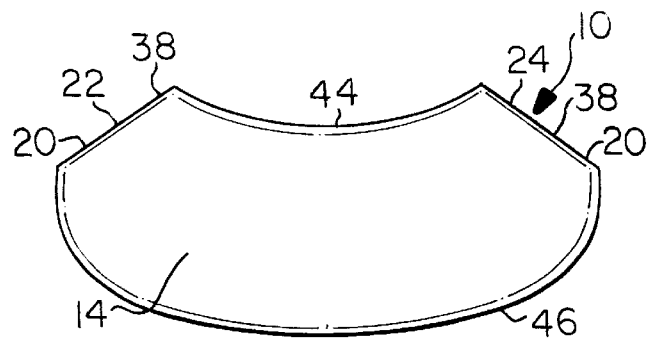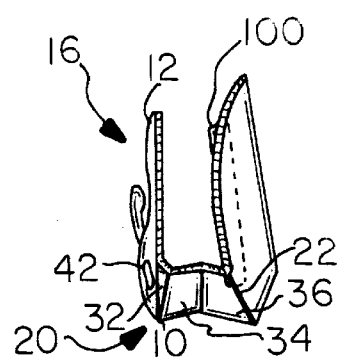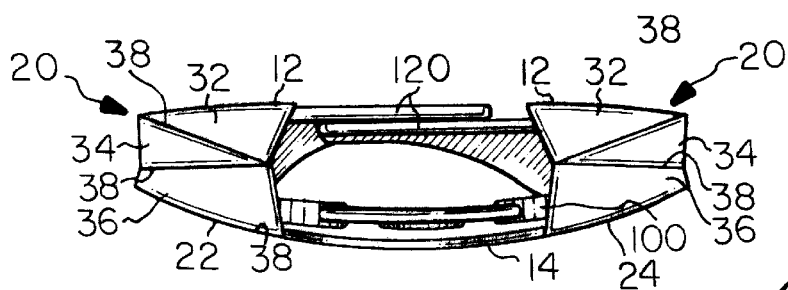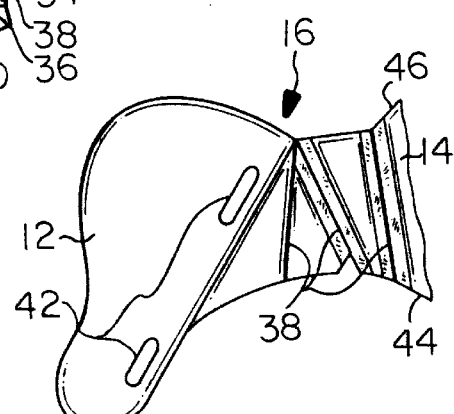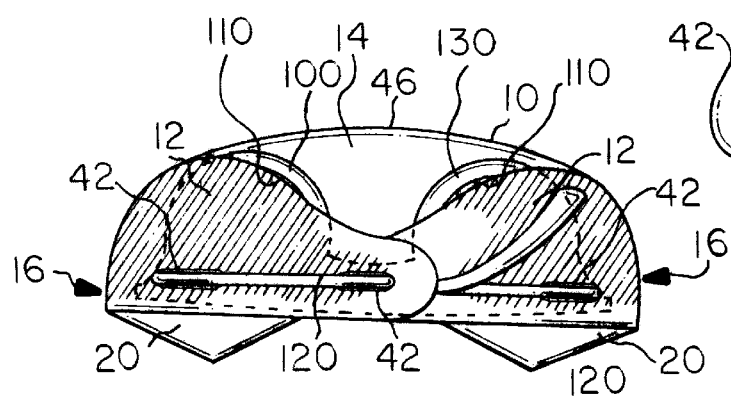

FOLDING VISOR AND CASE APPARATUS FOR EYEGLASSES

BACKGROUND OF THE INVENTION

1. Field of the Invention

The present invention relates generally to the field of eyeware and eye protection devices. More specifically the present invention relates to a folding visor and case apparatus for eyeglasses including two substantially rigid side panels, a substantially rigid sun shield panel extending between the side panels and a linkage panel assembly connecting each side panel to an end of the sun shield panel. The side panels each have eyeglass arm attachment means so that the eyeglasses and the visor apparatus can be operationally interconnected to open and close in unison. When opened, the apparatus deploys the sun shield panel outwardly and over the eyeglass lenses to function as a visor, and when closed the apparatus envelopes the eyeglasses to function as a protective case. The linkage panel assemblies taken in conjunction with substantially rigid sun shield and side panels are a key inventive feature of the apparatus, because they provide full sun shield panel deployment, entirely out of the direct field of vision of the wearer.

2. Description of the Prior Art

There have been a variety of eyeglass visor designs created over the years. Cassel, U.S. Pat. No. 5,553,321, issued on Sep. 10, 1996, teaches a visor and case device for use in combination with eyeglasses. Cassel includes a bill portion constructed of two overlying layers of flexible material that form a pocket for receiving a folded pair of eyeglasses. The visor is generally U-shaped, and is curved downwardly at each side to define an upwardly arched middle sun shield portion and two integral temple covering side portions. An upright slot is provided in each side portion to receive and pass an eyeglass arm. As a result of the longitudinally curved and vertically arched elongate shape of the visor, pivoting the visor side portions outwardly by opening the eyeglass arms raises the bill portion. Pivoting the visor side portions inwardly by closing the eyeglass arms against the lens frame lowers the bill portion to toward the lenses. A problem with Cassel is that the continuous and uniform side portion and bill portion construction limits the extent to which the bill portion can deploy outwardly and rise through the action of opening the eyeglass arms. The Cassel bill portion deforms together with the rest of the device during deployment and remains partially within the wearer direct field of vision. Furthermore, the provision of a pocket for the eyeglasses suggests that the protective coverage achieved by folding by folding Cassel is inadequate.

Some prior devices include visors which removably fit onto or around eyeglasses, but which do not double as protective cases. Garbutt, U.S. Pat. No. 4,543,667, issued on Oct. 1, 1995, reveals a sun visor for attachment to a pair of eyeglass arms. Garbutt includes a bill member formed of a flat, rigid stiffening member having a concave inner edge and convex outer edge and which is covered by fabric. Two elastic loops protrude from each end of the bill member for snugly receiving eyeglass arms to mount to the visor. Landis, U.S. Pat. No. 4,945,573, issued on Aug. 7, 1990, discloses a visor and shield devices attached to eyeglasses. Landis includes a crescent-shaped visor having ports at its ends for engagingly receiving eyeglass arms so that the visor protrudes outwardly over the eyeglass lenses. An upright transparent face shield is also provided, having upwardly projecting tabs which engagingly fit into slits along the visor forward edge, so that the face shield hangs from the visor. Burns, U.S. Pat. No. 4,606,453, issued on Aug. 19, 1986, reveals an eyeglass visor and case. The Burns device is similar to that of Landis, except that the visor is constructed of two layers of material defining between them a pocket for receiving the folded eyeglasses. A problem with Burns is that the wearer first must remove the device from the eyeglass arms before folding the arms, and then must place the folded eyeglasses into the visor pocket. Furthermore this procedure must be reversed to deploy the visor. Carr, U.S. Pat. No. 5,113,529, issued on May 19, 1992, reveals an eyeglass visor and retainer device. The Carr device is a visor of pliable material having a series of slits on each side through which eyeglass arms are woven.

Other prior devices include protective side panels with eyeglass arm passing slots, but do not incorporate sun visor portions. One is Gardner, U.S. Pat. No. 5,339,119, issued on Aug. 16, 1994 for an eye protector device including a foam rubber-like resilient insert member. Gardner includes what are essentially goggles in which eyeglasses fit, so that the eyeglass lenses align with goggle lens ports. The resilient insert member has lens apertures and fits between the eyeglass frame and the goggles to seal around the lenses and between the goggles and the wearer face. As a result, only minimal amounts of air can pass between the eyeglass frame and the goggles. The wearer eyes are shielded from wind, snow and rain, and yet the minimal air reaching lenses allegedly keeps them from fogging. Griffin, U.S. Pat. No. 5,388,269, issued on Feb. 14, 1995, discloses an eye shielding apparatus. Griffin includes two temple area shield members which are manufactured as a single piece and separated for use along a frangible line. Each shield member has a series of eyeglass arm passing slots for snug fitting around an eyeglass arm, and shield member end segments for bending inwardly toward the nearest lens to more fully cover the lens peripheral area.

Tatar, U.S. Pat. No. 5,299,682, issued on Apr. 5, 1994, reveals an eyeglasses storage and protection device that can secure eyeglasses to the head of the wearer. Tatar includes a flexible pouch for receiving and storing the eyeglasses, with pouch closure means. Flexible strip portions extend from opposing ends of the pouch and have elastic end loops. When the eyeglasses are removed from the pouch for use, the pouch is coiled around its longitudinal axis and fastened into the spooled configuration, and the free end of each eyeglass arm is fitted snugly into one of the end loops. Then the device serves to secure the eyeglasses by wrapping around the back of the wearer head so that they do not fall forwardly off the wearer face. A problem with Tatar, like Gardner and Griffin, is that it does not provide a sun shielding visor function.

It is thus an object of the present invention to provide an visor apparatus for eyeglasses which removably attaches to the eyeglasses and which also functions as a protective carrying case.

It is another object of the present invention to provide such an apparatus which converts from a visor to a carrying case automatically, by wrapping around and unwrapping from around the eyeglasses, as the wearer folds and unfolds the eyeglass arms.

It is still another object of the present invention to provide such an apparatus in which the sun shielding portion pivots outwardly into its functional position as the eyeglass arms are opened, to an extent that the sun shielding portion is substantially perpendicular to and elevated above the eyeglass lenses for full and unobstructed vision through the lenses.

It is finally an object of the present invention to provide such an apparatus which is durable, compact and inexpensive to manufacture.

SUMMARY OF THE INVENTION

The present invention accomplishes the above-stated objectives, as well as others, as may be determined by a fair reading and interpretation of the entire specification.

A folding visor and case apparatus is provided for eyeglasses which include an eyeglass lens frame containing eyeglass lenses and eyeglass arms hingedly connected to the eyeglass lens frame, including two substantially rigid side panels; a substantially rigid sun shield panel extending between the side panels and having two sun shield panel lateral ends; a hinged linkage panel assembly connecting each of the side panels to a lateral end of the sun shield panel, each of the linkage panel assemblies including a series of at least first and last panel sections interconnected with hinges, the first panel section in the series being pivotally connected to an edge of one of the side panels and the last panel section in the series being pivotally connected at one of the sun shield panel lateral ends; where the side panels each include an eyeglass arm attachment structure for operationally interconnecting the eyeglasses and the apparatus to open and close substantially in unison, so that opening the apparatus deploys the sun shield panel over the eyeglass lenses to function as a visor and closing the apparatus causes the side and sun shield panels to envelope the eyeglasses to function as a protective case.

The first panel section is preferably wedge-shaped to transmit motion at an angle, and is mounted with a hinge to swing inwardly only, and the last panel section is preferably mounted with hinge to swing outwardly only; so that swinging the side panels outwardly from the sun shield panel twists each assembly and causes each assembly to buckle at the hinges, so that the last panel section pivots into an upright position and thereby elevates the sun shield panel. The sun shield panel lateral ends are preferably angled relative to the longitudinal axis of the sun shield panel. The hinges interconnecting the panel sections optionally include flexible material extending between the panel sections and fastened to the faces of the panel sections. The eyeglass arm attachment structures preferably include two eyeglass arm ports in each of the side panels for receiving and passing an eyeglass arm. The sun shield panel is preferably substantially crescent-shaped.

A folding visor and case apparatus is further provided for eyeglasses including an eyeglass lens frame containing eyeglass lenses and eyeglass arms hingedly connected to the eyeglass lens frame, including two substantially rigid side panels; a substantially rigid sun shield panel extending between the side panels and having two sun shield panel lateral ends; a resilient, flexible strip connecting each of the side panels to a lateral end of the sun shield panel; where the side panels each include an eyeglass arm attachment structure for operationally interconnecting the eyeglasses and the apparatus to open and close substantially in unison, as above described.

BRIEF DESCRIPTION OF THE DRAWINGS

Various other objects, advantages, and features of the invention will become apparent to those skilled in the art from the following discussion taken in conjunction with the following drawings, in which:

FIG. 3 is a front view of the apparatus in the closed configuration.

FIG. 4 is a top view of the apparatus of FIG. 3.

FIG. 5 is a rear view of the apparatus of FIG. 3.

FIG. 6 is an end view of the apparatus of FIG. 3.

FIG. 7 is a broken-away, close-up view of an end of the apparatus showing the optional flexible fabric hinges.

DETAILED DESCRIPTION OF THE PREFERRED EMBODIMENTS

Figure 1:
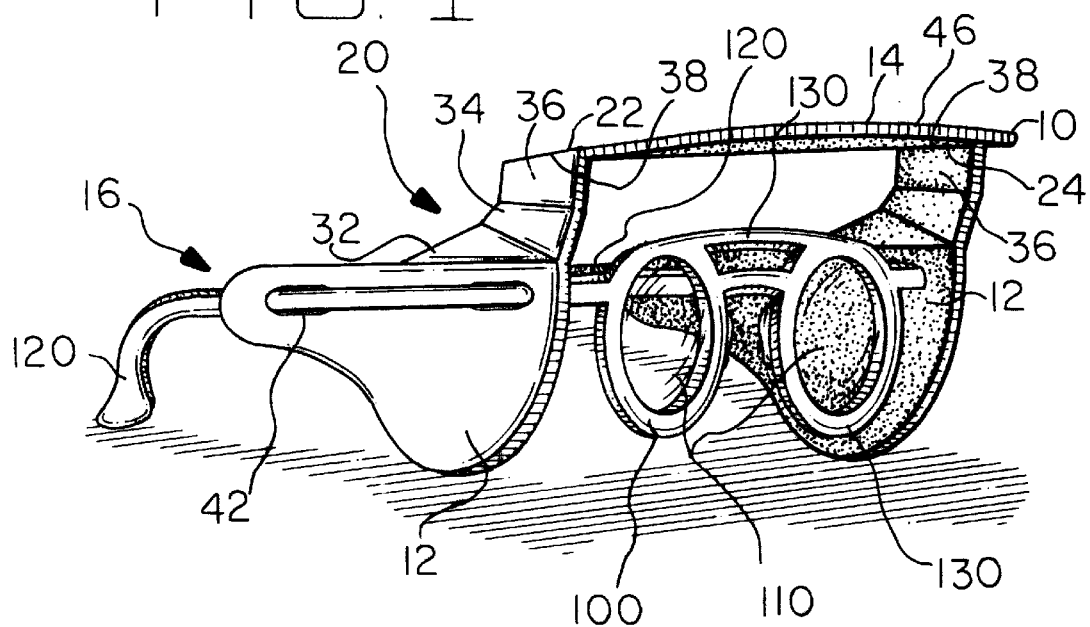
FIG. 1 is a perspective view of the first embodiment of the apparatus fitted onto an open pair of eyeglasses.
Figure 2:
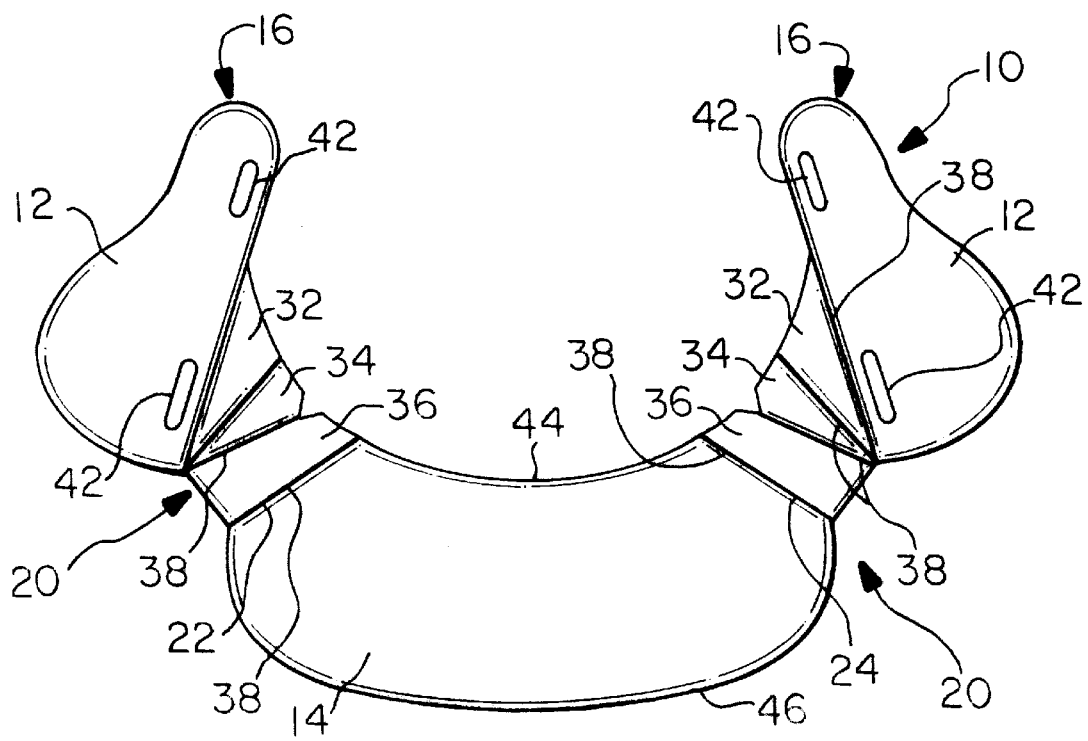
FIG. 2 is a plan view of the apparatus spread into a planar form.
Figure 8:
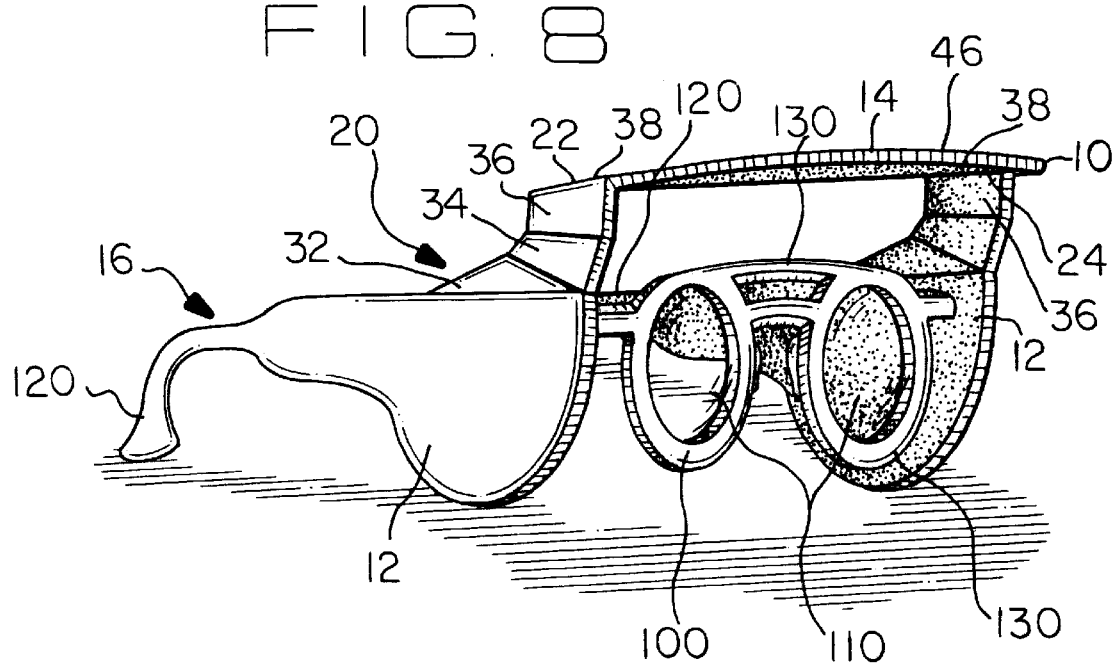
FIG. 8 is a view as in FIG. 1, but showing the alternative unified eyeglass arm and side panel structure.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Referring to FIGS. 1–8, a folding visor and case apparatus 10 is disclosed, including two rigid or semi-rigid side panels 12, a sun shield panel 14 extending between side panels 12 and a linkage panel assembly 20 connecting each side panel 12 to a lateral end of the sun shield panel 14. Side panels 12 each have eyeglass arm attachment means 16 so that the eyeglasses 100 and apparatus 10 are operationally interconnected to open and close in unison. When opened, apparatus 10 deploys sun shield panel 14 outwardly and above the eyeglass lenses 110 to function as a visor, and when closed apparatus 10 envelopes the eyeglasses 100 to function as a protective case. See FIG. 1.

Linkage panel assemblies 20 taken in conjunction with substantially rigid sun shield and side panels 14 and 12, respectively, are a key inventive feature of apparatus 10, and preferably each include a series of hingedly interconnected, substantially rigid panel sections 32, 34 and 36. See FIGS. 1 and 2. Sun shield panel 14 preferably terminates in angled lateral ends 22 and 24. See FIG. 3. The first panel section 32 in the series is pivotally connected to the upper edge of the adjacent side panel 12 and the last panel 36 in the series is pivotally connected to a sun shield panel lateral end 22 or 24. First panel section 32 is preferably wedge-shaped to transmit motion at an angle, and panel sections 32 and 34 are preferably hinged to swing inwardly only. Last panel section 36 is preferably hinged to swing outwardly only. Swinging side panels 12 outwardly into positions parallel to each other twists the respective assemblies 20 and causes the panel section series to buckle and pivot at hinges 38, so that the last panel section 36 pivots into an upright position to elevate sun shield panel 14. At this moment, the forward ends of the panel section hinges 38 are in compression and the rearward ends of the panel section hinges 38 are in tension, pivoting the forward end of the sun shield panel 14 upwardly so that sun shield panel 14 is oriented in a horizontal position. See FIG. 1. Third panel sections 36 also pivot 14 substantially upright to elevate sun shield panel 14 relative to eyeglass lenses 110.

Panel section hinges 38 are preferably formed of flexible material extending between panel sections 32, and side and sun shield panels 12 and 14, respectively, and glued to the panel and panel section faces. See FIG. 7.

The eyeglass arm attachment means 16 preferably include two arm ports 42 in each side panel 12 for receiving and removably engaging the arms 120 of a pair of eyeglasses 100. Ports 42 are preferably elongate slots which are wider at their forward ends. Sun shield panel 14 is preferably crescent-shaped, having a concave inner edge 44 and convex outer edge 46. Eyeglass arm attachment means 16 may alternatively attach the apparatus 10 to eyeglasses 100 permanently, such as with glue tied lines or other means, and may or may not include arm ports 42. Still alternatively, apparatus 10 and eyeglasses 100 may be a single unified structure, such as by making each side panel 12 and its corresponding eyeglass arm 120 from one and the same single unified piece of material. See FIG. 8. The claims should be read to cover both removable and permanent apparatus 10 attachment, as well as full unification of apparatus 10 and eyeglasses 100 as one structure, unless the claim language specifically states otherwise.

Apparatus 10 is inventively constructed so that opening the arms 120 of the eyeglasses 100 also swings the side panels 12 into position for placement adjacent to the wearer temples, and at the same moment automatically swings sun shield panel 14 into an outwardly extended sun shielding position. See FIG. 1. By the same token, folding the arms 120 of eyeglasses 100 against the back of the lens frame 130 also folds side panels 12 against the frame 130, and automatically swings the sun shield panel 14 downward and flat against the front of lens frame 130. See FIGS. 3–6.

Second Preferred Embodiment

Figure 9:
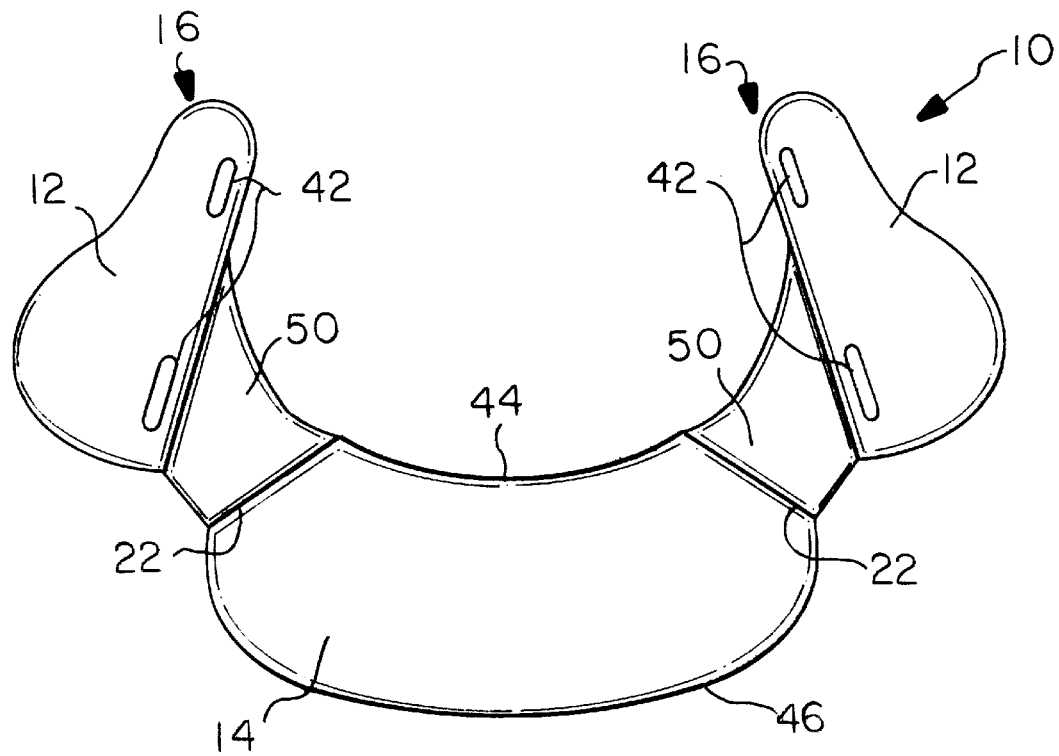
FIG. 9 is a view as in FIG. 2 of the second embodiment.

An alternative to linkage panel assemblies 20 is contemplated in the form of a resilient rubbery strip 50, having the same overall shape and configuration an assembly 20. See FIG. 9. Twisting the rubbery strip 50 by pivoting side panels 12 raises and lowers sun visor panel 14 in the same way that twisting assemblies 20 does. The remainder of apparatus 10 is unchanged.

This alternative is analogous but not equivalent to the panel section assemblies 20, because strip 50 does not swing fully upright at its ends, as panel section 36 does.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A folding visor and case apparatus for eyeglasses including an eyeglass lens frame containing eyeglass lenses and eyeglass arms hingedly connected to the eyeglass lens frame, comprising:

two substantially rigid side panels;

a substantially rigid sun shield panel extending between said side panels and having two sun shield panel lateral ends;

a hinged linkage panel assembly connecting each said side panel to a lateral end of said sun shield panel, each said linkage panel assembly comprising a series of at least first and last panel sections interconnected with a hinge, said first panel section in said series being pivotally connected to an edge of one said side panel and said last panel section in the series being pivotally connected at one said sun shield panel lateral end;

wherein said side panels each comprise eyeglass arm attachment means for operationally interconnecting the eyeglasses and said apparatus to open and close substantially in unison, such that opening said apparatus deploys said sun shield panel over the eyeglass lenses to function as a visor and closing said apparatus causes said side and sun shield panels to envelope the eyeglasses to function as a protective case.

2. The apparatus of claim 1, wherein said first panel section is wedge-shaped to transmit motion at an angle, and is hinged with a hinge to swing inwardly only, and wherein said last panel section is hinged with a hinge to swing outwardly only;

such that swinging said side panels outwardly from said sun shield panel twists each said assembly and causes each said assembly to buckle at said a hinge, such that said last panel section pivots into an upright position and thereby elevates said sun shield panel.

3. The apparatus of claim 2, wherein said sun shield panel lateral ends are angled relative to the longitudinal axis of said sun shield panel.

4. The apparatus of claim 2, wherein a hinge interconnecting said panel sections comprise flexible material extending between said panel sections and fastened to the faces of said panel sections.

5. The apparatus of claim 1, wherein said eyeglass arm attachment means comprise two eyeglass arm ports in each said side panel for receiving and passing an eyeglass arm.

6. The apparatus of claim 2, wherein said sun shield panel is substantially crescent-shaped.

7. A folding visor and case apparatus for eyeglasses including an eyeglass lens frame containing eyeglass lenses and eyeglass arms hingedly connected to the eyeglass lens frame, comprising:

two substantially rigid side panels;

a substantially rigid sun shield panel extending between said side panels and having two sun shield panel lateral ends;

a resilient, flexible strip connecting each said side panel to a lateral end of said sun shield panel;

wherein said side panels each comprise eyeglass arm attachment means for operationally interconnecting the eyeglasses and said apparatus to open and close substantially in unison, such that opening said apparatus deploys said sun shield panel over the eyeglass lenses to function as a visor and closing said apparatus causes said side and sun shield panels to envelope the eyeglasses to function as a protective case.

8. A folding visor and case apparatus:

an eyeglass lens frame containing eyeglass lenses;

an eyeglass arm comprising two rigid side panels and being hingedly connected to the eyeglass lens frame;

a substantially rigid sun shield panel extending between said side panels and having two sun shield panel lateral ends;

a hinged linkage panel assembly connecting each said side panel to a lateral end of said sun shield panel, each said linkage panel assembly comprising a series of at least first and last panel sections interconnected with a hinge, said first panel section in said series being pivotally connected to an edge of one said side panel and said last panel section in the series being pivotally connected at one said sun shield panel lateral end;

such that pivoting said eyeglass arm to open said apparatus deploys said sun shield panel over the eyeglass lenses to function as a visor and pivoting said eyeglass arm means to close said apparatus causes said side and sun shield panels to envelope the eyeglass lenses to function as a protective case.

\* \* \* \* \*